(12) United States Patent
Prevost et al.

(10) Patent No.: US 8,202,301 B2
(45) Date of Patent: Jun. 19, 2012

(54) DYNAMIC SPINAL ROD AND IMPLANTATION METHOD

(75) Inventors: Julien J. Prevost, Memphis, TN (US); Jeff R. Justis, Germantown, TN (US); Henry K. Bonin, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 344 days.

(21) Appl. No.: 12/429,329

(22) Filed: Apr. 24, 2009

(65) Prior Publication Data

US 2010/0274288 A1    Oct. 28, 2010

(51) Int. Cl.
*A61B 17/70* (2006.01)

(52) U.S. Cl. ........ 606/258; 606/257; 606/259; 606/260; 606/279

(58) Field of Classification Search .......... 606/246–279; 403/50–51, 134
See application file for complete search history.

(56) References Cited

U.S. PATENT DOCUMENTS

| | | |
|---|---|---|
| 4,164,045 A | 8/1979 | Bokros et al. |
| 4,850,999 A | 7/1989 | Planck |
| 5,116,360 A * | 5/1992 | Pinchuk et al. ............ 623/11.11 |
| 5,366,504 A | 11/1994 | Andersen |
| 5,375,823 A | 12/1994 | Navas |
| 5,413,598 A | 5/1995 | Moreland |
| 5,480,401 A | 1/1996 | Navas |
| 5,540,688 A | 7/1996 | Navas |
| 5,562,737 A | 10/1996 | Graf |
| 5,674,276 A | 10/1997 | Andersen |
| 5,961,516 A | 10/1999 | Graf |
| 6,042,592 A | 3/2000 | Schmitt |
| 6,375,662 B1 | 4/2002 | Schmitt |
| 7,029,475 B2 | 4/2006 | Panjabi |
| 7,166,131 B2 * | 1/2007 | Studer et al. ............... 623/17.16 |
| 7,291,150 B2 | 11/2007 | Graf |
| 7,326,210 B2 | 2/2008 | Jahng et al. |
| 7,476,238 B2 | 1/2009 | Panjabi |
| 7,655,026 B2 * | 2/2010 | Justis et al. ................... 606/259 |
| 7,776,075 B2 * | 8/2010 | Bruneau et al. ............... 606/279 |
| 7,811,309 B2 * | 10/2010 | Timm et al. .................... 606/257 |
| 7,854,752 B2 * | 12/2010 | Colleran et al. ............. 606/279 |
| 7,942,905 B2 * | 5/2011 | Lim et al. ....................... 606/257 |
| 2003/0055494 A1 | 3/2003 | Bezuidenhout et al. |
| 2003/0111147 A1 * | 6/2003 | Keener et al. ................. 148/671 |
| 2003/0191470 A1 | 10/2003 | Ritland |
| 2003/0199992 A1 | 10/2003 | Schmitt |
| 2004/0236329 A1 | 11/2004 | Panjabi |
| 2005/0085815 A1 * | 4/2005 | Harms et al. .................... 606/61 |
| 2005/0131405 A1 | 6/2005 | Molz et al. |
| 2005/0171540 A1 | 8/2005 | Lim et al. |
| 2005/0171543 A1 | 8/2005 | Timm et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0203519 A1 * | 9/2005 | Harms et al. .................... 606/61 |
| 2005/0222569 A1 | 10/2005 | Panjabi |

(Continued)

*Primary Examiner* — Eduardo C Robert
*Assistant Examiner* — Jan Christopher Merene (57) ABSTRACT

Embodiments of the invention include a system and method for stabilizing a segment of a spinal column with a dynamic spinal rod having a shank, a stay, and a casing sized to stretch tightly between components of the dynamic spinal rod and provide a structural connection between the components.

24 Claims, 10 Drawing Sheets

U.S. PATENT DOCUMENTS

| | | |
|---|---|---|
| 2005/0245930 A1 | 11/2005 | Timm et al. |
| 2005/0288670 A1 | 12/2005 | Panjabi et al. |
| 2006/0015100 A1 | 1/2006 | Panjabi |
| 2006/0022426 A1 | 2/2006 | Clive-Smith |
| 2006/0036240 A1* | 2/2006 | Colleran et al. ............... 606/61 |
| 2006/0142852 A1 | 6/2006 | Sowinski et al. |
| 2006/0247637 A1* | 11/2006 | Colleran et al. ............... 606/61 |
| 2007/0043356 A1 | 2/2007 | Timm et al. |
| 2007/0191841 A1 | 8/2007 | Justis et al. |
| 2007/0233073 A1 | 10/2007 | Wisnewski et al. |
| 2007/0270814 A1 | 11/2007 | Lim et al. |
| 2008/0154307 A1* | 6/2008 | Colleran et al. ............... 606/257 |
| 2008/0183213 A1* | 7/2008 | Veldman et al. ............... 606/257 |
| 2008/0255560 A1* | 10/2008 | Myers et al. .................... 606/63 |
| 2009/0099608 A1* | 4/2009 | Szczesny ....................... 606/257 |

\* cited by examiner

DYNAMIC SPINAL ROD AND IMPLANTATION METHOD

FIELD OF THE INVENTION

The present invention relates generally to the field of medical implants and methods of implanting medical implants, and more particularly relates to a dynamic spinal rod and methods of implanting the dynamic spinal rod.

BACKGROUND

Various pathologies of the human spine may be treated by stabilizing the joints of the spine. A traditional approach has been to rigidly fix joints of the spine through a number of surgical techniques and approaches. More recently, therapies have been developed to restore proper spacing of the spinal anatomy without more drastically affecting the natural motion of the spine by rigidly fixing or fusing one or more spinal joints. These therapies are sometimes referred to as motion preserving or dynamic, or as joint replacements, when specific joints such as joints between vertebral bodies or facet joints are replaced or treated. However, there remains a significant need to effectively mimic the natural load bearing and dynamic characteristics of the complex structure of the human spine.

A significant challenge associated with implementing dynamic systems is providing adequate fixation to the anatomy while simultaneously mimicking characteristics of the spine under various loading and motion conditions such as flexion, extension, and lateral bending. It may be particularly challenging to design a system that can support all loads developed over full ranges of flexion, extension, and lateral bending. The pedicle portions of vertebrae have traditionally provided excellent points to connect spinal rod and screw fixation systems because the pedicles include significant amounts of cortical bone into which a screw may be effectively placed. However, the posterior portion of the spine supported by fixation systems using pedicle screws is not the predominant natural load bearing structure of an anatomically correctly functioning spine. Therefore, a dynamic system that relies on pedicle screws may need a dynamic device connecting between the pedicle screws that is capable of responding non-linearly to loads applied in order to appropriately shares load with anterior portions of the spine. A need exists for improved pedicle-based implants that may be capable of both supporting a full range of anatomical loads developed over various degrees of flexion, extension, and lateral bending and sharing loads with anterior portions of connected vertebrae in a physiologically appropriate manner.

SUMMARY

One embodiment of the invention is a dynamic spinal rod. The dynamic spinal rod embodiment includes a shank with a first end configured to be coupled with a first pedicle screw, an opposite second end, and an intermediate section between the first end and the second end. The embodiment also includes a stay configured to be coupled with a second pedicle screw, the stay being slideably coupled along the shank. The dynamic spinal rod may include a casing that is coupled with the intermediate section of the shank and coupled to the stay. The casing of some embodiments is sized to stretch tightly between the shank and the stay and provide a structural connection between the shank and the stay when the stay is near the second end of the shank, and sized to extend loosely between the shank and the stay when the stay is moved closer to the first end of the shank.

Another embodiment of the invention is a system for stabilizing a segment of a spinal column. The system may include a first pedicle screw configured to attach to a spinal column, a second pedicle screw configured to attach to a spinal column, and a dynamic spinal rod. Embodiments of the dynamic spinal rod include a shank with a first end coupled to the first pedicle screw, an opposite second end, and an intermediate section between the first end and the second end. The dynamic spinal rod may also include a stay coupled to the second pedicle screw, the stay being slideably coupled along the shank, and the dynamic spinal rod may include a casing. In some embodiments, the casing is coupled with the intermediate section of the shank and coupled to the stay, the casing being sized to stretch tightly between the shank and the stay and provide a structural connection between the shank and the stay when the stay is near the second end of the shank and sized to extend loosely between the shank and the stay when the stay is moved closer to the first end of the shank.

Yet another embodiment of the invention is a method of stabilizing a spinal column that may include implanting a first screw in a first vertebral body, implanting a second screw in a second vertebral body, coupling between the first screw and the second screw a dynamic spinal rod, and injecting a material between the shank and the stay to dampen contracting movement of the dynamic spinal rod. The dynamic spinal rod may include a shank with a first end coupled to the first pedicle screw, an opposite second end, and an intermediate section between the first end and the second end, and a stay coupled to the second pedicle screw, the stay being slideably coupled along the shank. The dynamic spinal rod may also include a casing coupled with the intermediate section of the shank and coupled to the stay, the casing being sized to stretch tightly between the shank and the stay and provide a structural connection between the shank and the stay when the stay is near the second end of the shank and sized to extend loosely between the shank and the stay when the stay is moved closer to the first end of the shank.

DETAILED DESCRIPTION

Figure 1:
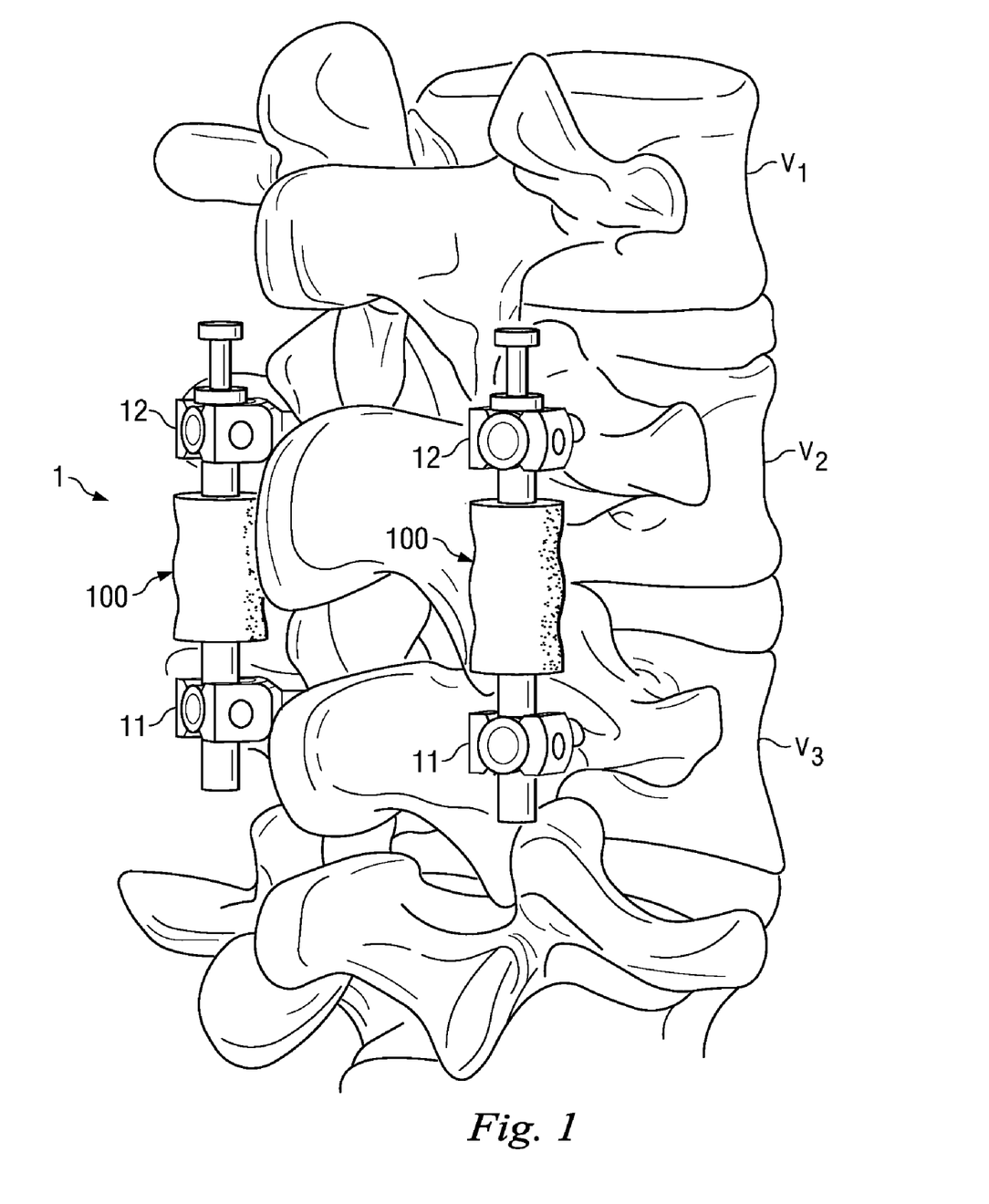
FIG. 1 is a perspective view of embodiments of a dynamic spinal stabilization system implanted in a portion of a lumbar region of a spine.

A system 1 for stabilizing a segment of a spinal column is illustrated in FIG. 1. Three vertebral bodies $V_1$, $V_2$, and $V_3$ are shown with the system 1 attached to the vertebral bodies $V_2$, and $V_3$. The system 1 includes two dynamic spinal rods 100, each attached to the vertebral bodies $V_3$ and $V_2$ respectively with a first pedicle screw 11 and a second pedicle screw 12. Each of the dynamic spinal rods 100 is shown in a partially expanded state in FIG. 1. In FIGS. 2, 3, 6, 10, 13, 18 and 19, embodiments of dynamic spinal rods are shown in a mostly unexpanded or contracted state. In FIGS. 4, 5, 7, and 14 embodiments of the dynamic spinal rods are shown in a mostly expanded state. The pedicle screws 11, 12 may be of any effective type capable of connecting with a vertebra. First and second pedicle screws 11, 12 illustrated may particularly be CD HORIZON® LEGACY™ top-loading pedicle screws supplied by Medtronic, Inc. Pedicle screws for use with the embodiments of FIGS. 10-23 include screws that include posts, such as TSRH-3D® Pedicle Screws and TSRH® OSTEOGRIP™ Pedicle Screws supplied by Medtronic, Inc.

The dynamic spinal rod 100 illustrated in FIGS. 2-5 includes a shank 110 with a first end 111 coupled with the first pedicle screw 11, an opposite second end 112, and an intermediate section 115 between the first end 111 in the second end 112. The shank 110 is a first diameter between the first end 111 and intermediate section 115. In the illustrated embodiment, the first diameter is approximately 5.5 mm and is round in cross-section. In other embodiments, the first diameter may be any effective diameter or shape, including but not limited to, diameters that step between different sizes, smoothly tapered diameters, or shapes that provide for particular fixation mechanisms with a pedicle screw. The shank 110 is a second diameter smaller than the first diameter between the intermediate section 115 and the second end 112. In the illustrated embodiment, the second diameter is approximately 2 mm and round in cross-section. In other embodiments, the second diameter may be any effective diameter or shape, including but not limited to, diameters that step between different sizes or smoothly tapered diameters. Non-limiting examples of shapes which the shank 110 may comprise are disclosed in U.S. Pat. Appl., Publication No. 2007/0191841, entitled, "Spinal Rods Having Different Flexural Rigidities about Different Axes and Methods of Use" which is hereby incorporated by reference in its entirety herein.

The shank 110 may be made from any biocompatible material. For example and without limitation, the shank 110 may include in whole or in part: non-reinforced polymers, reinforced polymers, metals, ceramics and combinations of these materials. Reinforcing of polymers may be accomplished with carbon, metal, or glass fibers or any other effective fiber material. In some embodiments, the shank 110 includes sections of bone or other tissues. Tissue materials include, but are not limited to, autograft, allograft, or xenograft, and may be resorbable or non-resorbable in nature. Examples of other tissue materials include connective tissues, demineralized bone matrix, and combinations of these and other materials. Biocompatible polymers may be obtained from natural or synthetic sources. Examples of natural materials of which a polymer may be composed include collagen, elastin, silk, and demineralized bone matrix. Examples of biocompatible polymer materials include polyethylene, low density polyethylene, polymethylmethacrylate (PMMA), polyetheretherketone (PEEK), polyetherketoneketone (PEKK), and polyurethane. A biocompatible polymer may also include a polymeric hydroxyethylmethacrylate (PHEMA). Example biocompatible metals include stainless steel and other steel alloys, cobalt chrome alloys, tantalum, titanium, titanium alloys, titanium-nickel alloys such as Nitinol and other superelastic or shape-memory metal alloys.

At least a portion of the shank 110 in some embodiments is a relatively flexible material, such as but not limited to, PEEK or Nitinol. A flexible material may be advantageous in some embodiments to permit the shank 110 to be deformed under the influence of physiological loads. Deformation of the flexible material permits the dynamic spinal rod 100 to more closely follow the motion and load bearing characteristics of a natural spinal segment, including sharing load with anterior portions of the vertebrae, rather than dictating a more rigidly defined path of motion of a spinal segment in combination with a more rigid implant. By way of example, the center of rotation of a natural spinal segment may change under different degrees of flexion, extension, and lateral bending, and under axial and shear loading. A more flexible shank 110 is able to bend and permit the dynamic spinal rod 100 to deform along a curvilinear or even compound curvilinear path without experiencing damage to the implant or compromising the implant's fixation to the bone. For instance, a shank 110 made from flexible material may assume an altered shape when opposite lateral loads are applied near the first end 111 and the second end 112 of the shank 110. In the illustrated embodiment, such opposite lateral loads may be transferred through the first pedicle screw 11 to the first end 111 and through the second pedicle screw 12 and a stay 120 to various points along the shank 110 between the intermediate section 115 and the second end 112. Embodiments of the stay 120 are described in more detail below.

The cross-sectional shape of the shank 110 illustrated is substantially round. In some embodiments, the cross-sectional shape may be altered to influence the amount or relative amount of load resisted, or the amount of deformation of the shank 110 in response to certain loadings. For example and without limitation, the cross-sectional shape of the shank 100 may be oval, triangular, rectangular, any other polygonal shape, or a non-symmetrical shape that provides more resistance to loading in one direction than it does in another direction.

The dynamic spinal rod 100 also includes a stay 120 coupled with the second pedicle screw 12. The stay 120 is coupled along the shank 110 such that the stay 120 may slide along the shank 110. The illustrated stay 120 is a collar that fits around the second diameter of the shank 110 and slides along the shank 110 between the intermediate section 115 and the second end 112. In other embodiments, the stay may be a collar that fits around or in cooperation with a shank and slides along a greater portion, or along substantially all of the shank. The stay 120 may be made from any biocompatible material such as those noted above with reference to the shank 110.

A stop in the form of a cap 113 is coupled to the second end 112 of the shank 110. As is more clearly depicted in FIGS. 3 and 5, the cap 113 is coupled to the second end 112 at least in part by a pin 114. In addition or alternatively, the cap 113 may be coupled to the second end 112 through use of an adhesive, melting, welding of an appropriate type, press fitting, or any effective mechanism. The cap 113 limits relative sliding between the stay 120 and the shank 110. Specifically in the illustrated case, the cap 113 prevents the stay 120 from sliding past the second end 112 of the shank 110. The position of the cap 113 or other stop may also be adjustable so that a user may select a maximum flexion for a device based on patient specific factors. Adjustment of a cap or stop may be accomplished pre-operatively, inter-operatively, or with the additional of additional minimally invasive instrumentation, post-operativley.

In some embodiments, a shank may include a notch in which a portion of a stay is configured to slide. By way of example, the shank and notch interface may be in the shape of a dovetail joint, a round section, a polygonal section, an interlocking of flat sections, any section including re-entrant angular cuts, or any combination of the specified example shapes. In some embodiments, a stay may include a notch in which a portion of a shank is configured to slide. Some embodiments may include any combination of notches and sliding components in both or either of a shank or a stay.

In some embodiments, the shank 110 and the stay 120 are sized such that the stay 120 will slide along or relative to the shank 110 for a distance greater than about 5 mm. Particularly, the shank 110 and the stay 120 may be capable of relative movements of about 5-15 mm. It may be significant for some embodiments to provide an adequate relative movement between the shank 110 and the stay 120 to enable more physiologically accurate dynamic implant systems. The range of flexion-extension motion permitted by some embodiments is about 3-20 degrees.

The dynamic spinal rod 100 may also include a casing 130 sized to be stretched tightly between the shank 110 and the stay 120 and provide a structural connection between the shank 110 and the stay 120 when the stay 120 is near the second end 112 of the shank 110. By designating that a casing under the invention be sized to be "stretched tightly" and "provide a structural connection" herein, it is meant that the casing react against a predominant portion of the load tending to urge apart a shank and a stay. The casing may also be described as dampening the dynamic spinal rod 100 when a patient in whom the device is implanted is in flexion. Other stops or limits such as the cap 113 may bear load as well, but the casing under various embodiments is more than a sealing mechanism or enclosure. The casing 130 may also be sized to extend loosely between the shank 110 and the state 120 when the state 120 is moved closer to the first end 111 of the shank 110. In the embodiment illustrated, the casing 130 is coupled with the intermediate section 115 of the shank 110 and coupled to the stay 120.

Figure 4:
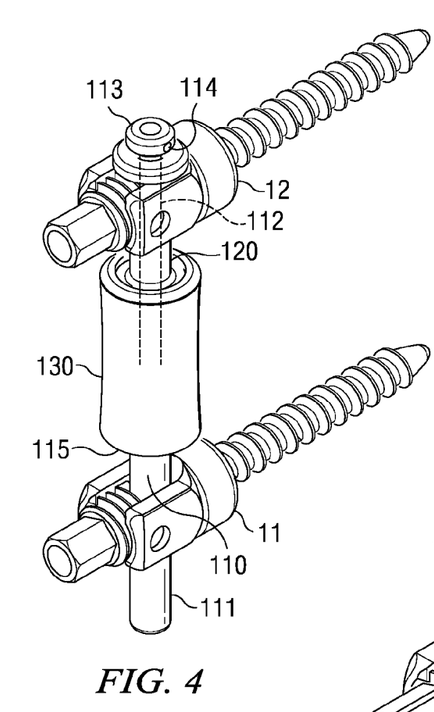
FIG. 4 is a perspective view of the dynamic spinal rod of FIG. 2 with the dynamic spinal rod in an expanded state.
Figure 5:
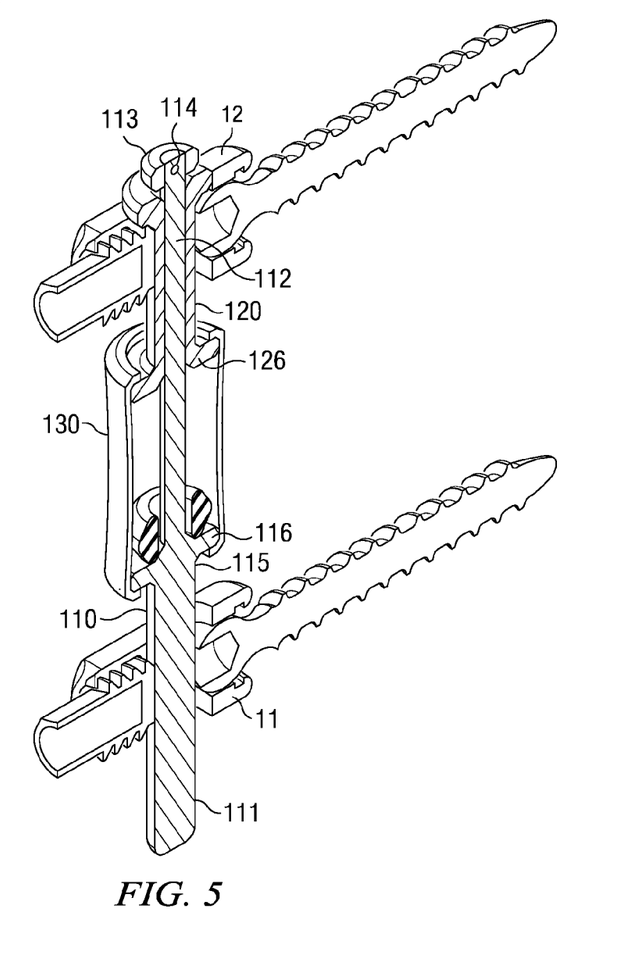
FIG. 5 is a cross-sectional view of the dynamic spinal rod of FIG. 4.
Figure 7:
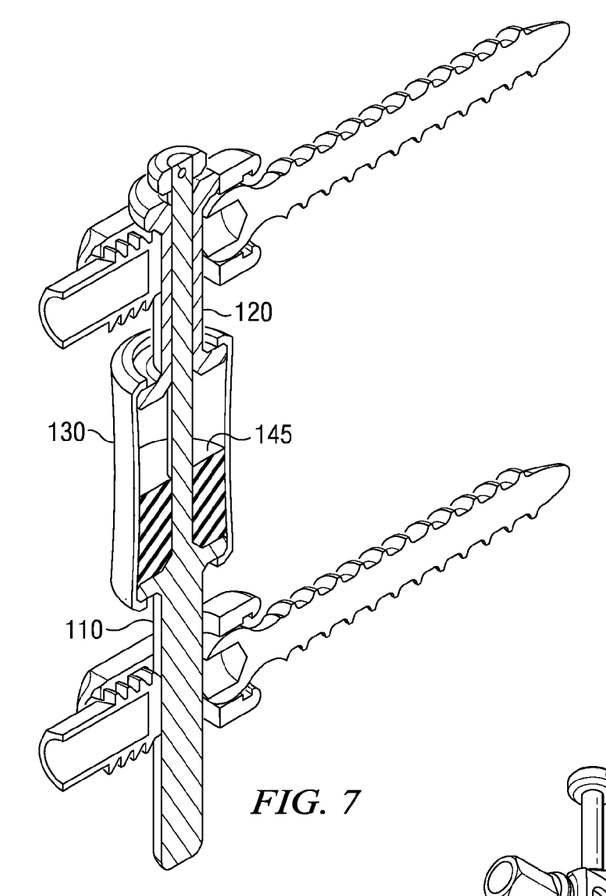
FIG. 7 is a cross-sectional view of the dynamic spinal rod of FIG. 6 with the dynamic spinal rod in an expanded state and additionally showing a material injected into the dynamic spinal rod.

The casing 130 illustrated in FIGS. 4, 5, and 7 is stretched tightly between the shank 110 and the stay 120 to provide a structural connection between the shank 110 and the stay 120. As more clearly illustrated in FIG. 5, the casing 130 is coupled with a flange 116 at the intermediate section 115 of the shank 110. The casing 130 is coupled with a flange 126 of the stay 120. The casing 130 may be coupled with one or both of the shank 110 and the stay 120 by any effective mechanism. By way of example and without limitation, effective mechanisms may include plastic or metal welding, ultrasonic welding, laser welding, melting, crimping, gluing, and stitching. The casing 130 may also be captured between another member and the shank 110 or the stay 120 to couple with the casing 130. For example and without limitation, a belt, band, or circular clamp may be used to capture the casing 130 against the shank 110 or the stay 120.

Figure 8:
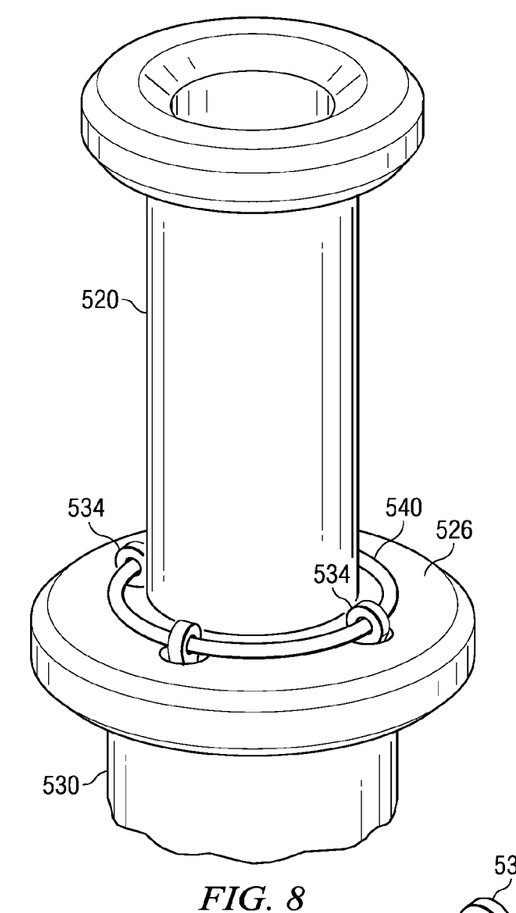
FIG. 8 is a perspective view of stay and casing components of embodiments of the dynamic spinal rod.
Figure 9:
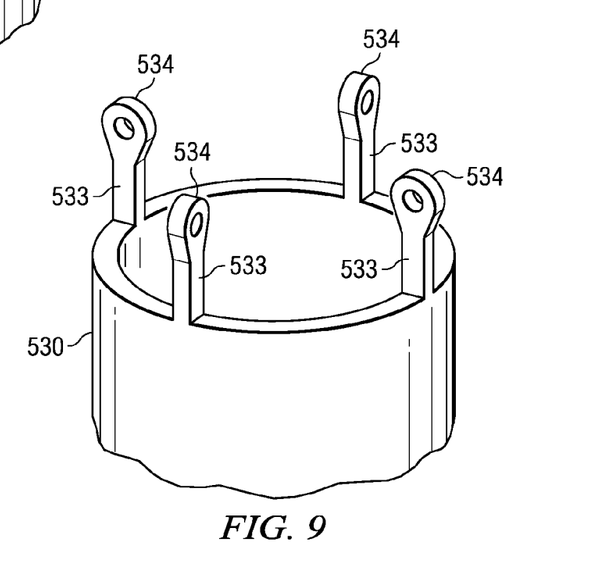
FIG. 9 is a perspective view of a portion of a casing as illustrated in FIG. 8.

FIGS. 8 and 9 illustrate one suitable device for coupling a casing 530 to a stay 520 that is similar to the stay 120. The casing 530 includes tethers 533 with eyelets 534. The tethers 533 are configured to extend through a portion of the stay 520. In the illustrated embodiment, the tethers 533 with eyelets 534 extend through a flange 526 in the stay 520. The tethers 533 with eyelets 534 in the illustrated embodiment are configured to receive a connection pin 540 to couple the casing 530 to stay 520. The connection pin 540 shown in FIG. 8 is a circular pin that extends through all four eyelets 534. However, in other embodiments a connection pin may include separate devices for each connected tether 533. The tethers 533 of the casing 530 may be formed from extensions of fibers of which the casing 530 is at least in part composed. For example, where the casing 530 is at least in part made from fibers that are braided or woven, all or some of those fibers may extend from the main body of the casing 530 and be assembled to form the tethers 533. A similar coupling may be made between the casing 530 and an appropriately configured shank similar to the shank 110.

Figures 2, 3:
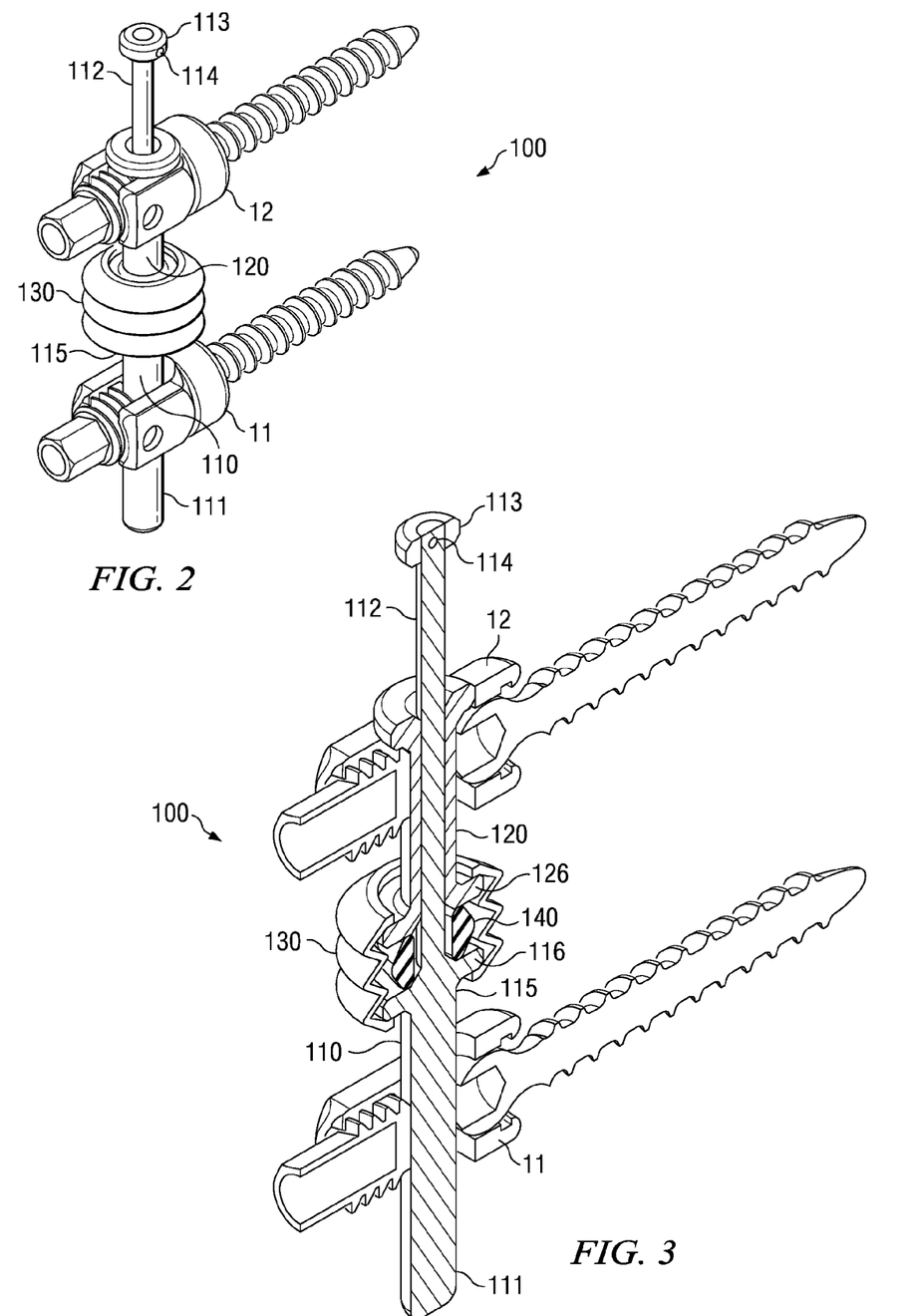
FIG. 2 is a perspective view of an embodiment of a dynamic spinal rod.
FIG. 3 is a cross-sectional view of the dynamic spinal rod of FIG. 2.
Figure 6:
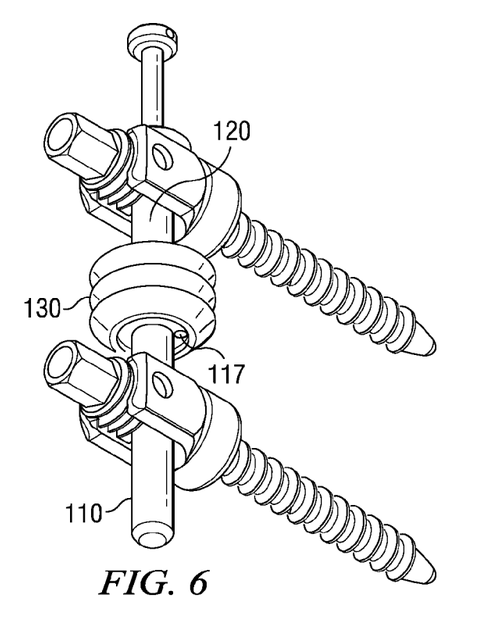
FIG. 6 is a perspective view of an embodiment of a dynamic spinal rod in a contracted state and viewed from a bottom perspective.

The casing 130 illustrated in FIGS. 2, 3, and 6 extends loosely between the shank 110 and the stay 120 when the stay 120 is moved closer to the first end 111 of the shank 110. The casing 130 extending loosely may have pleating, crimping, or gathered sections of material. Pleating, crimping, or gathering may be applied to the entire casing 130 or may be applied to one or more layers of a multi-layered casing, and may be maintained by the stiffness of the material, by chemical additive such as a resin, by stitching, or by any effective mechanism. In some embodiments, the stiffened pleating, crimping, or gathering may be completely straightened when the casing 130 is stretched tightly, but return to its original shape when the stretching force is removed. These stiffened portions may help keep loose material retracted and out of the way of functioning anatomical structures.

The casing 130 may include continuous tubular portions of material or may be woven, knitted, or braided from strands or other smaller component parts. The casing 130 may particularly be a woven, knitted, or braided tubular structure. The casing 130 may comprise a homogenous weave, or may comprise a fabric weave with anisotropic properties. In another embodiment, a casing 130 may be comprised of a non-woven, but flexible material. Whether woven or non-woven, the sheath may be formed from elastic, inelastic, semi-elastic material, or some combination of these or other materials. Materials which may be used for strands or fibers in the casing include but are not limited to titanium, memory-wire, ultra-high molecular weight polyethylene (UHMWPE), cross-linked UHMWPE, polytetrafluoroethylene (PTFE), ethylene chlorotetrafluoroethylene, fluorinated ethylene-propylene, and polyvinyl flouride. Exemplary elastic materials which may be used for some resilient components include polyurethane, silicone, silicone-polyurethane, polyolefin rubbers, hydrogels, and the like. Other suitable elastic materials may include Nitinol or other superelastic alloys. Further, combinations of superelastic alloys and non-metal elastic materials may be suitable to form elastic strands.

In some embodiments, the casing 130 includes multiple layers of material. Multiple layers of material may be advantageous in providing a strong and dense composite that does not elongate more under axial loading than would be appropriate to a design. A dense casing 130 may be useful in some embodiments to prevent growth of tissue into the casing 130, which could interfere with function of the dynamic spinal rod 100. In some embodiments, one layer of the casing 130 is particularly dense to serve as a layer against penetration of the casing 130 by tissue or other sources. Designs may also require controlled resistance by the casing 130 to axial loads applied over a relatively long zone of displacement, which multiple layer material may be effective in providing.

In embodiments of the casing 130 with multiple layers, a bonding material may be used between two or more of the multiple layers to join all or a part of the casing 130 together as a composite body. The bonding material may be any material effective to join all or a part of the various layers with one another. By way of non-limiting example, the bonding material may be an adhesive, a polycarbonate urethane, or a PTFE material that melts during a heat process to bond layers. Useful heating or laminating conditions for a PTFE bonding material may include temperatures from about 300° C. to about 400° C. for a period of about 5 minutes to 30 minutes. Fibers or strands of bonding material such as PTFE may also be woven into fabric from which the casing 130 is made. After processing, such a fabric may be more durable and more resistant to rupture or tearing. Such a fabric may also be less likely to unravel at the level of individual fibers and, similarly, as a whole. In some embodiments, at least one of the multiple layers is a layer between at least two other layers that has a melting temperature that is lower than the immediately adjacent layers.

An embodiment of the invention includes a method of forming a structural casing comprising, providing first and second layers of a structural casing, providing a central layer of a structural casing with a melting temperature lower than a melting temperature of the first and second layers, and placing the central layer between the first and second layers, and exposing the structural casing to a temperature between about 300° C. and about 400° C. for a period of about 5 minutes to 30 minutes to melt the central layer and bond the first layer to the second layer. Some embodiments may further include coupling the structural casing between two components of a dynamic spinal rod connected at its opposite ends to separate vertebrae such that the structural casing resists movement of the vertebrae away from one another.

Some embodiments of a dynamic spinal rod 100 also include a bumper 140 between the shank 110 and the stay 120. As particularly shown in FIGS. 3 and 5, the bumper 140 is a cannulated member and is place around the shank 110. The bumper is located axially between the flange 116 at the intermediate section 115 of the shank 110 and the flange 126 of the stay 120. In this position, the bumper 140 may dampen contracting movement of the dynamic spinal rod 100. Particularly, as the bumper 140 is compressed between the flange 116 and the flange 126, the bumper 140 of some embodiments provides dampening of the compressing motion where the bumper 140 is made from a resilient material. The bumper 140 may be made from any resilient material. In some embodiments, the bumper 140 is a solid material. The bumper 140 may also comprise a fluid material, or may be placed as a liquid and then harden to a solid over time or as a result of some other stimulus, such as but not limited to, a second chemical part, heat, removal of heat, and electromagnetic energy. Non-limiting example materials from which a bumper may be made include silicone, silicone-polyurethane, polyurethane, polyolefin rubbers, hydrogels, Nitinol or other superelastic alloys, and a gas contained within a vessel or within various components of the dynamic spinal rod 100.

Additional and alternative features of the dynamic spinal rod 100 are illustrated in FIGS. 6 and 7. Specifically, a port 117 is shown in FIG. 6 through which material of a bumper 145 (FIG. 7) may be passed. The bumper 145 may be a fluid or hardenable liquid material as described above. The bumper 145 may also include multiple granular components that individually will fit through the port 117, but collectively make up a bumper 145 with resilient properties. Some embodiments also include a plug for blocking the port 117 after the bumper 145 has been placed within the dynamic spinal rod 100. The plug may be removable to facilitate altering the size or composition of the bumper 145 over time. Such a procedure may be accomplished directly or transcutaneously.

The dynamic spinal rod 200 illustrated in FIGS. 10-23 includes a shank 210 with a first end 211 configured to be coupled with a first pedicle screw, an opposite second end 212, and an intermediate section 215 between the first end 211 and the second end 212. The dynamic spinal rod 200 also includes a stay 220 configured to be coupled with a second pedicle screw. The stay 220 is coupled along the shank 210 such that the stay 220 may slide along the shank 210. Specifically in the illustrated embodiment, a distal end 222 of the stay 220 couples with and cooperatively slides along the second end 212 of the shank 210.

Figure 11:
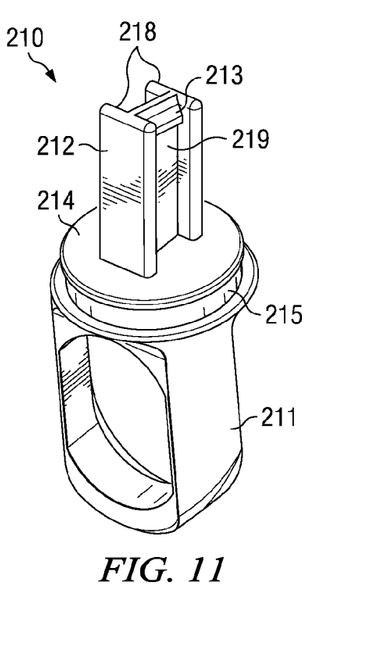
FIG. 11 is a top perspective view of a shank of the dynamic spinal rod illustrated in FIG. 10.
Figure 12:
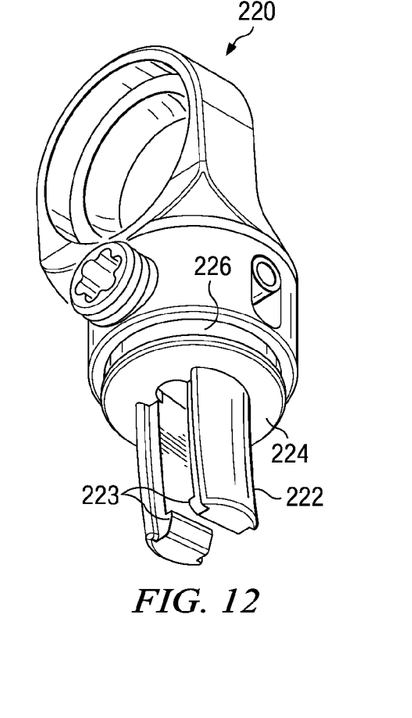
FIG. 12 is a bottom perspective view of a stay of the dynamic spinal rod illustrated in FIG. 10.

The shank 210, as illustrated in FIG. 11, includes a second end 212 that has an "H" cross-sectional shape. The "H" cross-sectional shape includes two flanges 218 and a web 219. A catch 213 is included on the web 219. Another catch 213 (not shown) may be located on the opposite side of the web 219. The stay 220, as illustrated in FIG. 12, includes a distal end 222 with two legs that cooperatively slide along the second end 212 of the shank 210. Each leg of the distal end 222 may include a hook 223 to engage with one or both catches 213 (FIG. 11) to limit relative sliding between the stay 220 and the shank 210. Specifically in the illustrated case, the catches 213 in combination with the hooks 223 prevent the stay 220 from sliding past the second end 212 of the shank 210 and thereby restrict flexion motion of a patient to a predetermined amount. More generally stated, both the shank 210 and the stay 220 include a combination of notches, re-entrant angular cuts, and protrusions that provide a sliding path for the shank 210 relative to the stay 220. In some embodiments, a shank may include a notch in which a portion of a stay is configured to slide. By way of example, the shank and notch interface may be in the shape of a dovetail joint, a round section, a polygonal section, an interlocking of flat sections, any section including re-entrant angular cuts, or any combination of the shapes. In some embodiments, a stay may include a notch in which a portion of a shank is configured to slide. Various embodiments may include any combination of notches and sliding components in both or either of a shank or a stay.

One or both of the shank 210 and the stay 220 may be made from any biocompatible material. For example and without limitation, the shank 210 or the stay 220 may include in whole or in part: non-reinforced polymers, reinforced polymers, metals, ceramics and combinations of these materials. Reinforcing of polymers may be accomplished with carbon, metal, or glass fibers or any other effective fiber material. In some embodiments, the shank 210 or the stay 220 include sections of bone or other tissues. Tissue materials include, but are not limited to, autograft, allograft, or xenograft, and may be resorbable or non-resorbable in nature. Examples of other tissue materials include connective tissues, demineralized bone matrix, and combinations of these and other materials. Biocompatible polymers may be obtained from natural or synthetic sources. Examples of natural materials of which a polymer may be composed include collagen, elastin, silk, and demineralized bone matrix. Examples of biocompatible polymer materials include polyethylene, low density polyethylene, PMMA, PEEK, PEKK, and polyurethane. A biocompatible polymer may also include a PHEMA. Example biocompatible metals include stainless steel and other steel alloys, cobalt chrome alloys, tantalum, titanium, titanium alloys, titanium-nickel alloys such as Nitinol and other superelastic or shape-memory metal alloys.

At least a portion of one or both of the shank 210 and the stay 220 in some embodiments is a relatively flexible material, such as but not limited to, PEEK or Nitinol. A flexible material may be advantageous in some embodiments to permit the shank 210 and the stay 220 to be deformed under the influence of physiological loads. Deformation of the flexible material permits the dynamic spinal rod 200 to more closely follow the motion and load bearing characteristics of a natural spinal segment, including sharing load with anterior portions of the vertebrae, rather than dictating a more rigidly defined path of motion of a spinal segment in combination with a more rigid implant. By way of example, the center of rotation of a natural spinal segment may change under different degrees of flexion, extension, and lateral bending, and under axial and shear loading. A more flexible shank 210 or stay 220 is able to bend and permit the dynamic spinal rod 200 to deform along a curvilinear or even compound curvilinear path without experiencing damage to the implant or compromising the implant's fixation to the bone. For instance, a shank 210 or a stay 220 made from flexible material may assume an altered shape when opposite lateral loads are applied through the first pedicle screw and the second pedicle screw. As specifically shown in the illustrated embodiment, flexible material included in one or both of the second end 212 of the shank 210 and the legs of the distal end 222 of the stay 220 will allow the path of expansion of the dynamic spinal rod 200 to be altered in response to applied loads.

Figure 13:
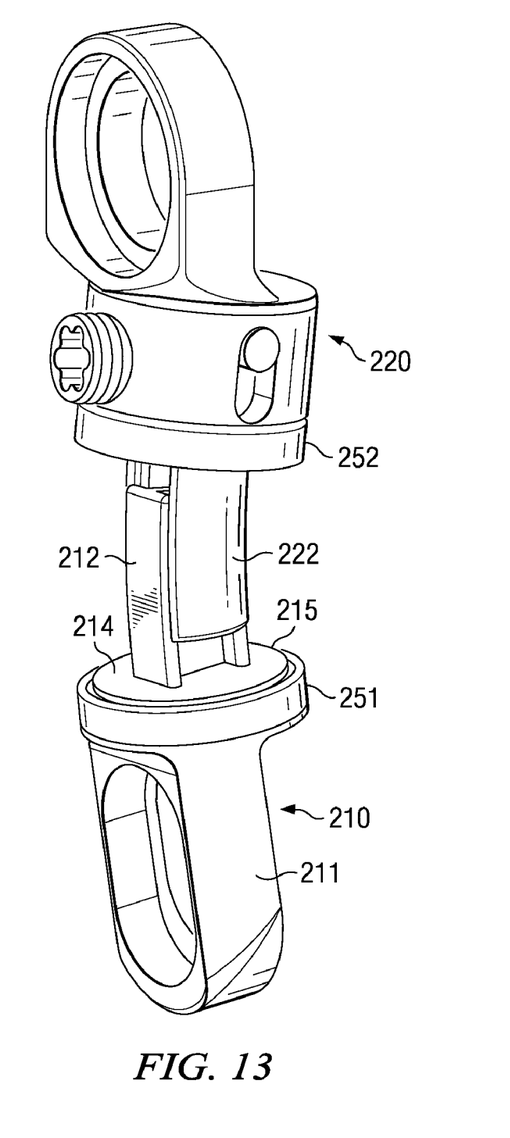
FIG. 13 is a perspective view of the dynamic spinal rod shown in FIG. 10 in a mostly contracted state with certain components removed for illustrative purposes.
Figure 14:
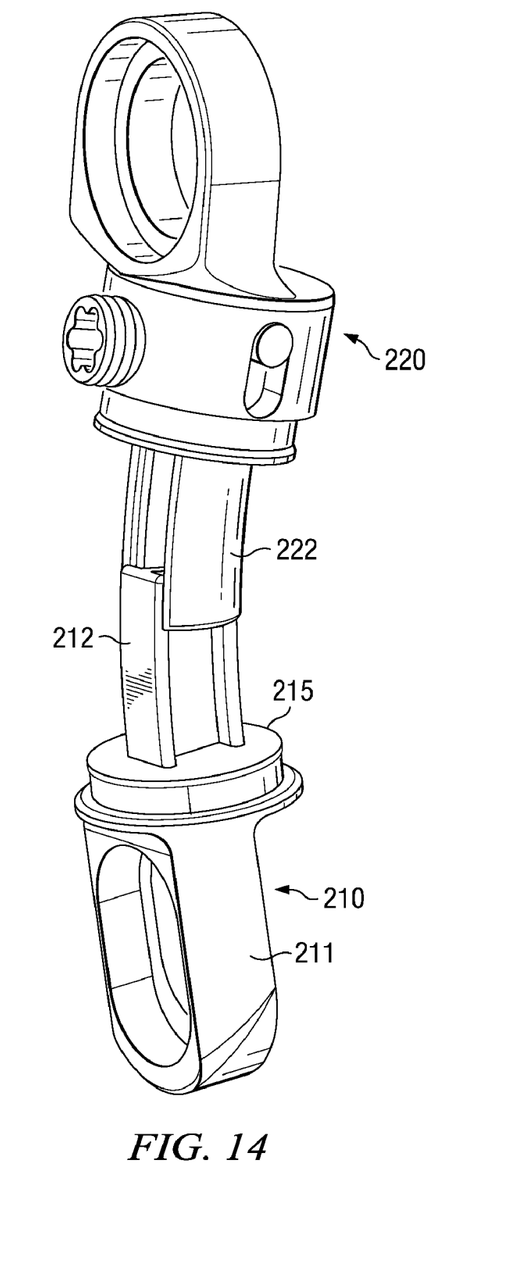
FIG. 14 is a perspective view of the dynamic spinal rod shown in FIG. 10 in a mostly expanded state with certain components removed for illustrative purposes.

The embodiment illustrated in FIGS. 10-23 demonstrates a dynamic spinal rod 200 with a kyphotic curvature. Particularly, the second end 212 of the shank 210 and the legs of the distal end 222 are curved with a kyphotic relationship to a spine on which the illustrated embodiment is designed to be implanted. The dynamic spinal rod 200 will follow a path of kyphotic curvature where expanded and contracted in embodiments that include rigid enough materials to dictate following the kyphotic path. This curvature permits some embodiments of the device to more accurately mimic the center of rotation of some naturally functioning lumbar spinal segments. In embodiments having more flexible materials, the path defined by the kyphotic curvature will be a reference path from which devices will deviate based on applied loads. FIG. 13 illustrates components of the dynamic spinal rod 200 as positioned when the dynamic spinal rod 200 is close to a fully contracted state. This state may result where a patient to which the device is attached is near an anatomical state of full extension. FIG. 14 illustrates components of the dynamic spinal rod 200 as positioned when the dynamic spinal rod 200 is close to a fully expanded state. This state may result where a patient to which the device is attached is near an anatomical state of full flexion.

In some embodiments, the shank 210 and the stay 220 are sized such that the stay 220 will slide along or relative to the shank 210 for a distance greater than about 5 mm. Particularly, the shank 210 and the stay 220 may be capable of relative movements of about 5-15 mm. It may be significant for some embodiments to provide an adequate relative movement between the shank 210 and the stay 220 to enable more physiologically accurate dynamic implant systems. The range of flexion-extension motion permitted by some embodiments is about 3-20 degrees.

Figure 10:
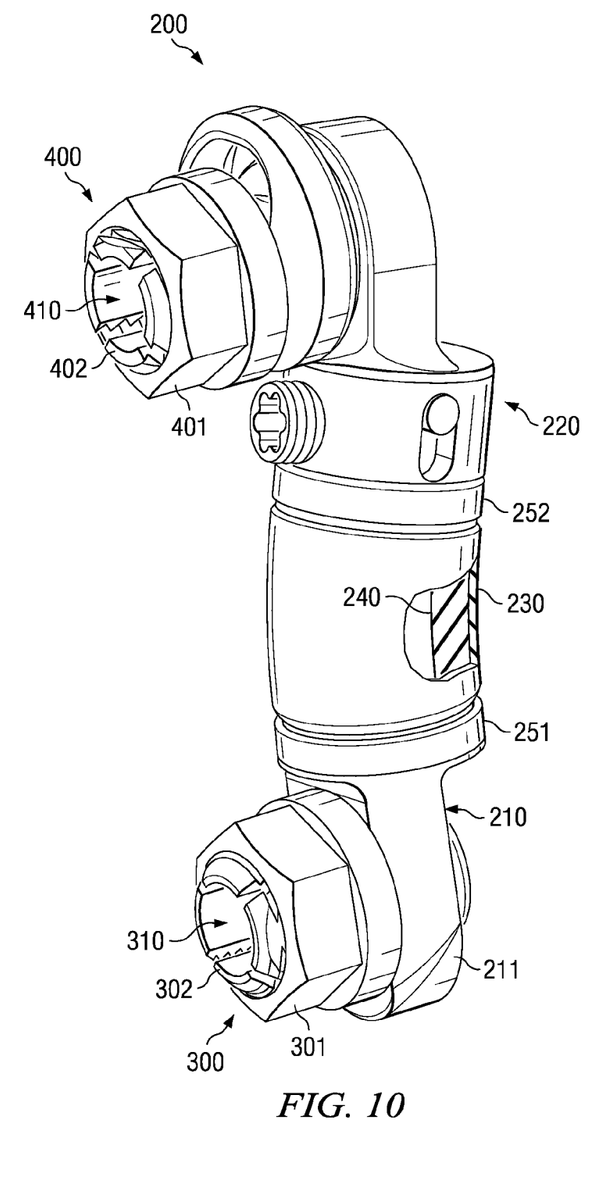
FIG. 10 is a perspective view of an embodiment of a dynamic spinal rod.
Figures 15, 16, 17, 18:
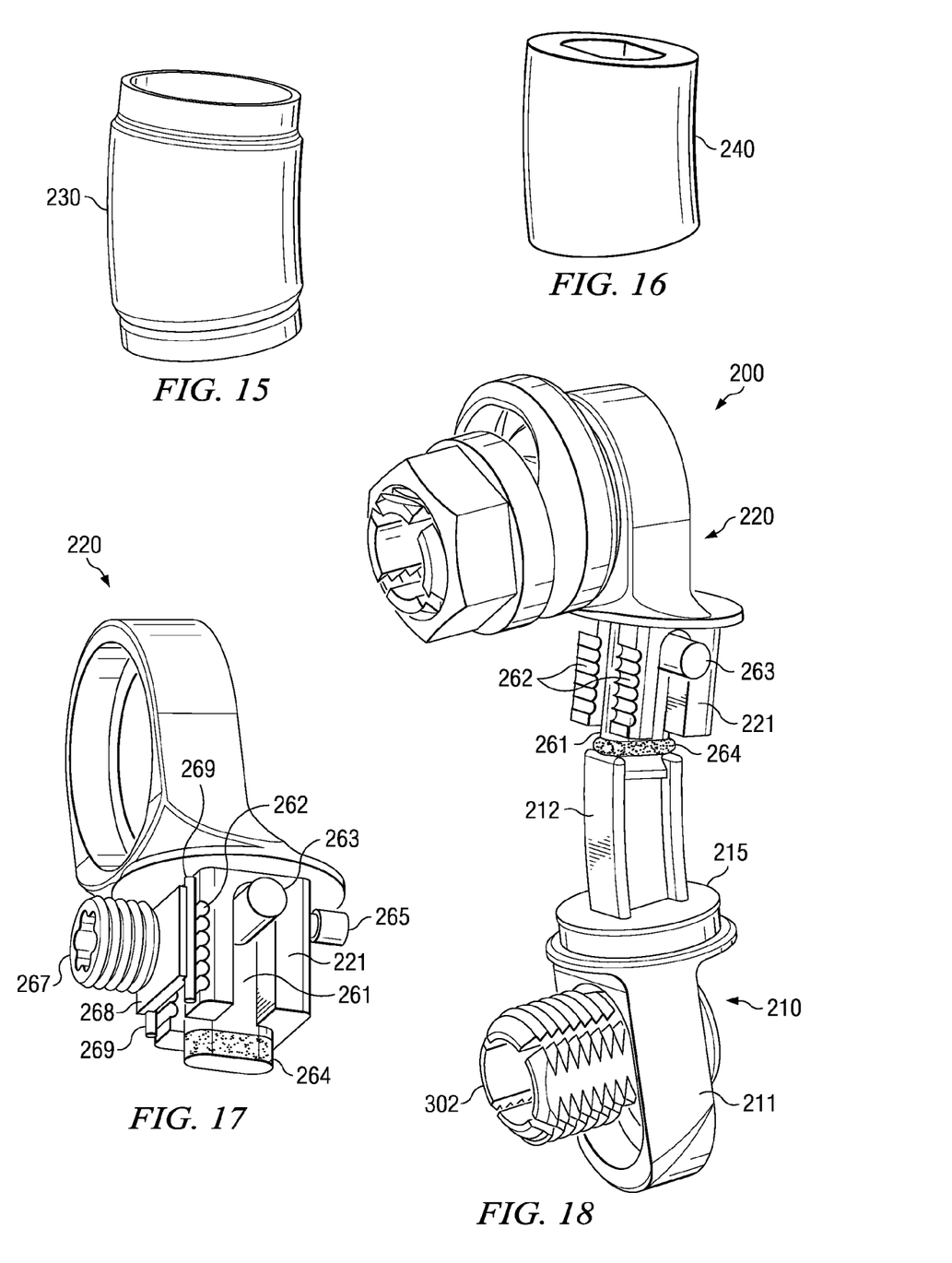
FIG. 15 is a perspective view of a casing of the dynamic spinal rod illustrated in FIG. 10.
FIG. 16 is a perspective view of a bumper of the dynamic spinal rod illustrated in FIG. 10.
FIG. 17 is a perspective view of the stay shown in FIG. 12 with certain components removed for illustrative purposes.
FIG. 18 is a perspective view of the dynamic spinal rod shown in FIG. 10 with certain components removed for illustrative purposes.

The dynamic spinal rod 200 may also include a casing 230, as shown in FIGS. 10 and 15, sized to be stretched tightly between the shank 210 and the stay 220 and provide a structural connection between the shank 210 and the stay 220 when the stay 220 is near the second end 212 of the shank 210. By designating that a casing under the invention be sized to be "stretched tightly" and "provide a structural connection" herein, it is meant that the casing react against a predominant portion of the load tending to urge apart a shank and a stay. The casing may also be described as dampening the dynamic spinal rod 200 when a patient in whom the device is implanted is in flexion. Other stops or limits such as the catches 213 and the hooks 223 may bear load as well, but the casing under various embodiments is more than a sealing mechanism or enclosure. The casing 230 may also be sized to extend loosely between the shank 210 and the state 220 when the state 220 is moved closer to the first end 211 of the shank 210. In the embodiment illustrated, the casing 230 is coupled with the intermediate section 215 (FIG. 11) of the shank 210 and coupled to the stay 220. The casing 230 illustrated in FIG. 10 is not begin stretched tightly between the shank 210 and the stay 220 because the illustrated dynamic spinal implant 200 is near a contracted state. However, further expansion of the dynamic spinal implant 200 would result in the casing being stretched tightly between the shank 210 and the stay 220 to provide a structural connection between the shank 210 and the stay 220. The structural connection between the shank 210 and the stay 220 would occur over a range of expansion.

The casing 230 illustrated in FIG. 10 is coupled at the intermediate section 215 (FIG. 11) of the shank 210. The casing 230 is coupled with a rim 226 (FIG. 12) of the stay 220. The casing 230 may be coupled with one or both of the shank 210 and the stay 220 by any effective mechanism. By way of example and without limitation, effective mechanisms may include plastic or metal welding, ultrasonic welding, laser welding, melting, crimping, gluing, and stitching. The casing 230 may also be captured between another member and the shank 210 or the stay 220 to couple with the casing 230. For example and without limitation, a belt, band, or circular clamp such as first and second bands 251, 252 may be used to capture the casing 230 against the shank 210 or the stay 220. The first and second bands 251, 252 may one or both be secured in place by a press fit, by use of an adhesive, by physically stretching and then releasing the bands, by use of pins or other fasteners through the bands, or by any other effective mechanism. In some embodiments, the casing 230 may extend loosely between the shank 210 and the stay 220.

As noted with reference to the casing 130, the casing 230 may have pleating, crimping, or gathered sections of material or any other configurations or features noted with reference to the casing 130 herein. Similarly, as noted with reference to the casing 130, the casing 230 may include any of the material compositions, configurations, or features of the casing 130.

Some embodiments of a dynamic spinal rod 200 also include a bumper 240 between the shank 210 and the stay 220. As particularly shown in FIGS. 10, 13, and 16, the bumper 240 is a cannulated member around the second end 212 of the shank 210 and the distal end 222 of the stay 220. Referring to FIGS. 10-13, and 16, the bumper 240 is positioned between a surface 214 of the shank 210 and a surface 224 of the stay 220. In this position, the bumper 240 may dampen contracting movement of the dynamic spinal rod 200. Particularly, as the bumper 240 is compressed between the surface 214 of the shank 210 and the surface 224 of the stay 220, the bumper 240 of some embodiments provides dampening of the compressing motion. The bumper 240 may be made from a resilient material. In some embodiments, the bumper 240 is a solid material. The bumper 240 may also comprise a fluid material, or may be placed as a liquid and then harden to a solid over time or as a result of some other stimulus, such as but not limited to, a second chemical part, heat, removal of heat, and electromagnetic energy. Non-limiting example materials from which a bumper may be made include silicone, silicone-polyurethane, polyurethane, polyolefin rubbers, hydrogels, Nitinol or other superelastic alloys, and a gas contained within a vessel or within various components of the dynamic spinal rod 200.

An embodiment of the stay 220 is illustrated in FIGS. 17-20 with certain components removed to better depict elements of a variable length adjustment. In some embodiments, the variable length adjustment includes a dampening device. A column 261 is shown coupled with a chassis 221 of the stay 220. Two projections 263 are fixed to the column 261 and extend past the periphery of the stay 220 such that the projections may be reached to move the column 261 relative to the chassis 221. In some embodiments, the projections 263 may be inside the periphery of the stay 220, but remain reachable to move the column, or the implant may function in the absence of the projections 263 by contacting the column 261 directly to apply a force. A guide pin 265 is shown in FIG. 17 that provides stabilization to the column 261 and maintains assembly of the construct in some embodiments.

Figures 19, 20:
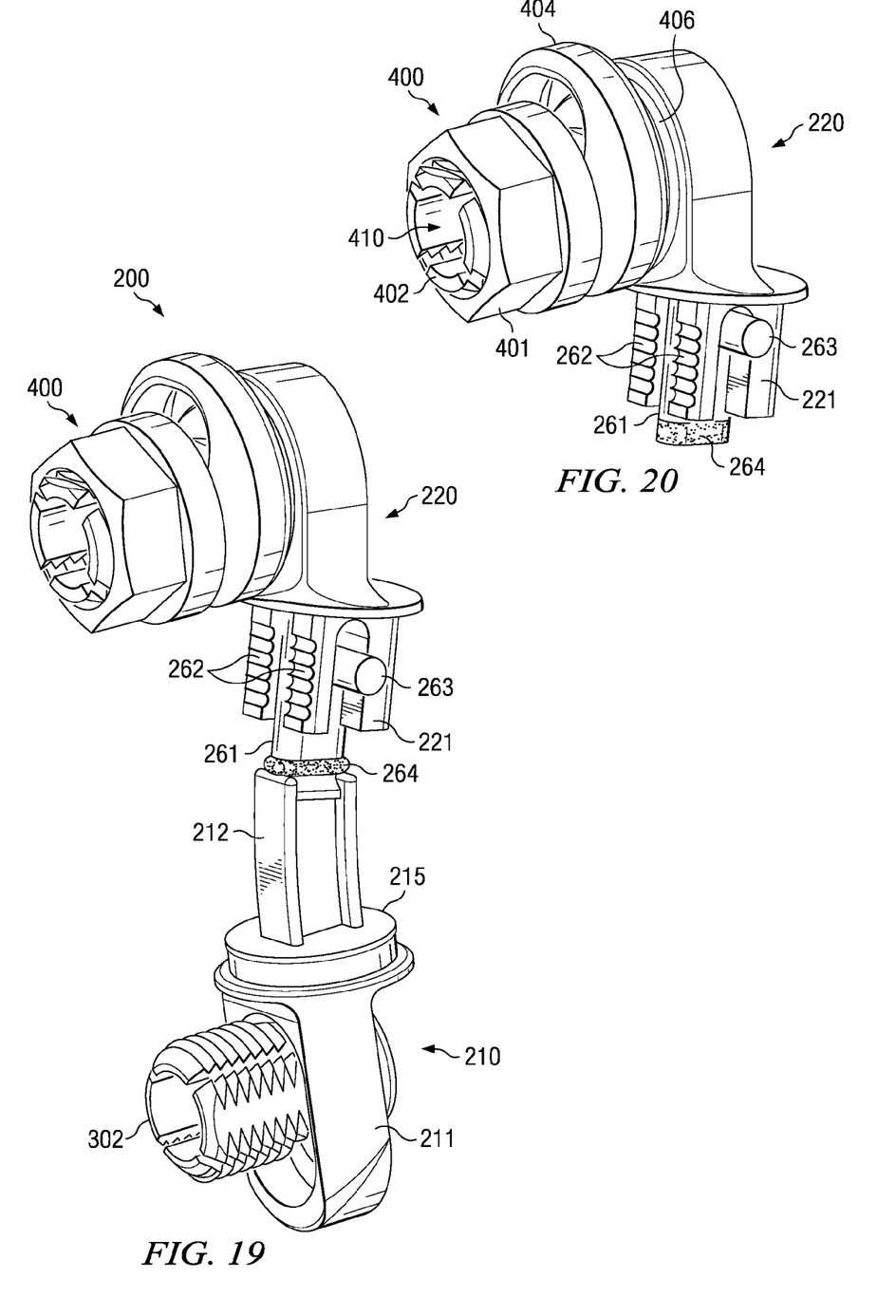
FIG. 19 is a perspective view of the dynamic spinal rod shown in FIG. 18 with the distance the shank and stay will slide relative to one another alternate by a variable length adjustment.
FIG. 20 is a perspective view of a variable angle connection mechanism for coupling a stay to a pedicle screw.
Figure 21:
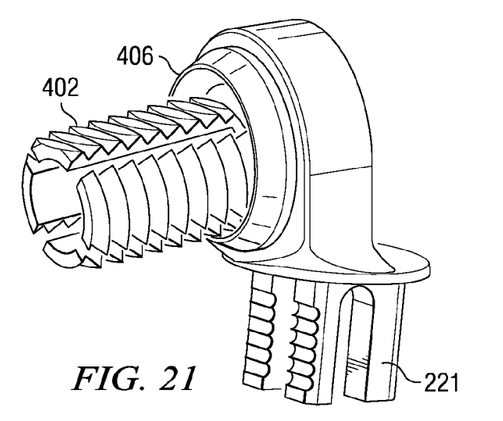
FIG. 21 is a perspective view of the variable angle connection mechanism of FIG. 20 with various components removed for illustrative purposes.
Figure 22:
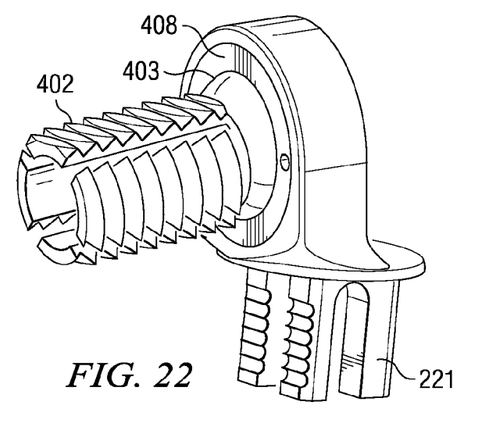
FIG. 22 is a perspective view of the variable angle connection mechanism of FIG. 20 with various components removed for illustrative purposes.

A cushion 264 is shown coupled to the column 261. The cushion 264 illustrated in FIGS. 17 and 20 is in an uncompressed or expanded state. The cushion 264 shown in FIGS. 18 and 19 is being compressed between the column 261 of the stay 220 and the second end 212 of the shank 210. Consequently, the cushion 264 contributes to dampening between the shank 210 and the stay 220, in addition to the bumper 240. Additionally, the column 261 and cushion 264 may provide a positive stop of movement of the shank 210 the stay 220 toward one another. When assembled, the stay 220 of the illustrated embodiment includes the column 261 and cushion 264 between the two legs of the distal end 222 of the stay 220 (FIG. 13).

The illustrated device creates a variable length adjustment by enabling different lengths of extension of the column 261 relative to the chassis 221. As shown in FIG. 18, the column 261 is almost fully drawn back into the chassis 221 so that the dynamic spinal rod 200 is configured to contract to an almost minimal height. In FIG. 19, the column 261 has been extended partially relative to the chassis 221. In operation, movement of the column 261 relative to the chassis 221 may be accomplished by applying forces to one or both of the projections 263. The column 261 may further be locked and unlocked relative to the chassis 221. By such a mechanism, selectively altered distances that the shank 210 and the stay 220 will slide relative to one another may be chosen by an implant user.

A mechanism for locking movement between the column 261 and the chassis 221 is illustrated in more detail in FIG. 17. Scallops 262 are illustrated on one surface of the chassis 221. The scallops 262 provide a surface against which increased friction is developed when an object is pressed against the surface. The surface could be any textured, abrasive, or roughened surface instead of or in addition to scallops, or in some embodiments may be a generally flat and smooth surface. A spring plate 268 is shown that is designed to receive force from a locking screw 267. The spring plate 268 in response exerts force on the press lock bars 269, and subsequently the scallops 262. The illustrated spring plate 268 is designed to bend near its middle in response to force from the locking screw 267 and come into contact with the column 261 to lock the column 261 relative to the chassis 221. Any other effective locking mechanism is contemplated under embodiments of the invention. For example, the locking screw 267 or an equivalent may contact the column 261 directly without a spring plate. The mechanism for applying the locking force may be a cam, clamp, pin, or any other effective mechanism.

The dynamic spinal rod 200 may be coupled to the spine with pedicle screws that include posts over which ends of the implant may be placed prior to tightening. The dynamic spinal rod 200 shown in FIG. 10 is connectable to posts through a fixed angle connector 300 and a variable angle connector 400. The fixed angle connector 300 shown includes a post clamp 302 with an opening 310 through which a post may be extended and a nut 301. When the nut 301 is tightened, the post clamp 302 is translated through the nut 301 and the opening 310 decreases in diameter to attach to a post of a pedicle screw. The angle of the post clamp 302 relative to the shank 210 is variable until the nut 301 is tightened. After tightening, the angle between the post clamp 302 and the shank 210 is fixed.

Figure 23:
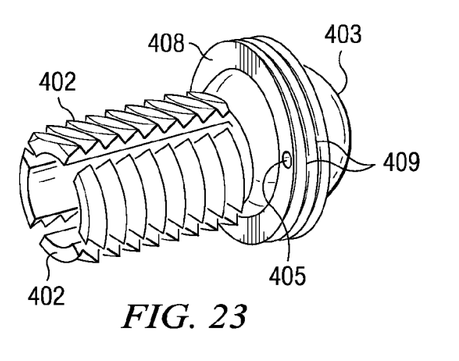
FIG. 23 is a perspective view of the variable angle connection mechanism of FIG. 20 with various components removed for illustrative purposes.

The variable angle connector 400 shown includes a post clamp 402 with an opening 410 through which a post may be extended and a nut 401. When the nut 401 is tightened, the post clamp 402 is translated through the nut 401 and the opening 410 decreases in diameter to attach to a post of a pedicle screw. Additional mechanisms of the variable angle connector 400 are illustrated in FIGS. 20-23. In FIG. 20, the nut 401 includes a built-in washer and sits against a hemispherical washer 404. The hemispherical washer 404 nests into a back washer 406. The back washer 406 includes an inner diameter that captures a spherical head 403 of the post clamp 402. A retainer 408 captures the spherical head 403 of the post clamp 402 and threads into the chassis 221. The retainer 408 of the illustrated embodiment includes a spherical surface that substantially matches a surface of the spherical head 403 of the post clamp 402. As seen in FIG. 23 the retainer 408 includes threads 409 configured to screw into the chassis 221. The retainer 408 in some embodiments may be screwed in place with a tool that fits in one or more sockets 405. Any other effective means of attaching the retainer 408 to the chassis 221 is contemplated under various embodiments.

In operation, when the nut 401 is turned, a pulling force is exerted on the post clamp 402 and a pushing force is exerted on the hemispherical washer 404. The hemispherical washer 404, in turn, transfers force to the back washer 406, and the back washer 406 comes into contact with and transfers force to a portion of the spherical head 403 of the post clamp 402. Consequently, as the nut 401 is turned and the post clamp 402 is tightened on to a pedicle screw post, the back washer 406 exerts pressure on the spherical head 403, but does not tighten the spherical head 403 relative to the retainer 408. The retainer 408 keeps the spherical head 403 fixed in all three spatial axes, but provides little or no rotational restraint. Therefore, some compensation is available to overcome any inaccurate directional placement of a pedicle screw when used with the variable angle connector 400. Additionally, some improved degree of lateral bending allowance is provided for with the variable angle connector 400.

In the illustrated embodiment, the superior connector is a variable angle connector 400 and the inferior connector is a fixed angle connector 300. However, in other embodiments the superior connector and inferior connector rotational degrees may be switched, or both connectors may be fixed angle connectors, or both connectors may be variable angle connectors.

An embodiment of the invention is a method of stabilizing a spinal column. Embodiments may include implanting a first screw in a first vertebral body and implanting a second screw in a second vertebral body and coupling the first screw and the second screw a dynamic spinal rod. For example, the first pedicle screw 11 and a second pedicle screw 12 may respectively be implanted in the vertebral bodies $V_3$ and $V_2$. In various embodiments, a dynamic spinal rod may be placed on one side of a spinal column at a single level, bilaterally as shown in FIG. 1, or unilaterally or bilaterally over two or more levels. The dynamic spinal rod placed under methods of the invention is exemplified in, but not limited to, the dynamic spinal rods 100, 200. Each of the dynamic spinal rods 100, 200 includes a shank with a first end coupled to the first pedicle screw, an opposite second end, and an intermediate section between the first end and the second end; a stay coupled to the second pedicle screw, the stay being slideably coupled along the shank; and a casing coupled with the intermediate section of the shank and coupled to the stay, the casing being sized to stretch tightly between the shank and the stay and provide a structural connection between the shank and the stay when the stay is near the second end of the shank and sized to extend loosely between the shank and the stay when the stay is moved closer to the first end of the shank.

Another act of a method embodiment is injecting a material between the shank and the stay to dampen contracting movement of the dynamic spinal rod. As noted with regard to the bumper 145 above, the injected material may be a fluid or hardenable liquid material or multiple granular components that collectively make up a bumper 145 with resilient properties. In some embodiments, the injected material is allowed to change properties to cure to a particular consistency over time or a specific stimulus is provided to lead to curing of the injected material.

Various method embodiments of the invention are described herein with reference to particular medical implants. However, in some circumstances, each disclosed method embodiment may be applicable to each of the medical implants, or to some other implant operable as disclosed with regard to the various method embodiments.

Terms such as top, bottom, side, anterior, posterior, height, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A dynamic spinal rod comprising:
    a shank with a first end configured to be coupled with a first pedicle screw, an opposite second end, and an intermediate section between the first end and the second end;
    a stay configured to be coupled with a second pedicle screw, the stay being slideably coupled along the shank;
    a casing composed of multiple layers of material that are bonded together, the casing coupled with the intermediate section of the shank and coupled to the stay, the casing being sized to stretch tightly between a portion of the shank and the stay and provide a structural connection between the shank and the stay when the stay is near the second end of the shank, and sized to extend loosely between a portion of the shank and the stay when the stay is moved closer to the first end of the shank; and
    a bumper comprising a material injected into the dynamic spinal rod between the shank and the stay to dampen contracting movement of the dynamic spinal rod.

2. The dynamic spinal rod of claim 1 wherein the shank and stay are sized such that the stay will slide along the shank for a distance greater than 5 mm.

3. The dynamic spinal rod of claim 1 wherein the shank includes a stop near the second end of the shank that prevents sliding of the stay past the stop.

4. The dynamic spinal rod of claim 3 wherein the stop is a cap coupled to the second end.

5. The dynamic spinal rod of claim 3 wherein the stop is adjustable so that the degree of flexion permitted by the dynamic spinal rod may be selected.

6. The dynamic spinal rod of claim 1 wherein the shank is a first diameter between the first end and the intermediate section, and is a second diameter smaller than the first diameter between the intermediate section and the second end, and the stay includes a collar that that fits around the second diameter and slides along the shank.

7. The dynamic spinal rod of claim 1 wherein the shank is a flexible material that may assume an altered shape when opposite lateral loads are applied near the first end of the shank and near the second end of the shank.

8. The dynamic spinal rod of claim 1 wherein the stay is a collar that fits around the shank and slides along the shank.

9. The dynamic spinal rod of claim 1 wherein the shank includes a notch in which a portion of the stay is configured to slide.

10. The dynamic spinal rod of claim 1 wherein the stay includes a notch in which a portion of the shank is configured to slide.

11. The dynamic spinal rod of claim 1, further comprising a variable length adjustment that is configured to selectively alter the distance the shank and stay will slide relative to one another.

12. The dynamic spinal rod of claim 11 wherein the variable length adjustment includes an actuating mechanism and a lock.

13. The dynamic spinal rod of claim 1 wherein at least one layer is made from a tubular knitted, woven, or braided material.

14. The dynamic spinal rod of claim 1 wherein at least one layer is a dense layer resistant to tissue ingrowth.

15. The dynamic spinal rod of claim 1 wherein at least one of the multiple layers is a layer between at least two other layers that has a melting temperature that is lower than the immediately adjacent layers.

16. The dynamic spinal rod of claim 1 wherein the casing includes one or more tethers configured to extend through a portion of the stay to receive one or more connection pins to couple the casing to the stay.

17. The dynamic spinal rod of claim 16 wherein the tethers of the casing are formed by extensions of multiple fibers of which the casing is at least in part composed.

18. The dynamic spinal rod of claim 1 wherein the bumper is positioned between the intermediate section of the shank and the stay.

19. The dynamic spinal rod of claim 1 wherein the material injected into the dynamic spinal rod is designed to be cured in place.

20. A system for stabilizing a segment of a spinal column comprising:
 a first pedicle screw configured to attach to a spinal column;
 a second pedicle screw configured to attach to a spinal column; and
 a dynamic spinal rod comprising:
 a shank with a first end coupled to the first pedicle screw, an opposite second end, and an intermediate section between the first end and the second end,
 a stay coupled to the second pedicle screw, the stay being slideably coupled along the shank,
 a casing comprising of multiple layers of material that are bonded together, the casing coupled with the intermediate section of the shank and coupled to the stay, the casing being sized to stretch tightly between a portion of the shank and the stay and provide a structural connection between the shank and the stay when the stay is near the second end of the shank and sized to extend loosely between a portion of the shank and the stay when the stay is moved closer to the first end of the shank; and
 a bumper comprising a material injected into the dynamic spinal rod between the shank and the stay to dampen contracting movement of the dynamic spinal rod.

21. The system for stabilizing a segment of a spinal column of claim 20 wherein the shank is coupled to the first pedicle screw with a variable angle connection.

22. The system for stabilizing a segment of a spinal column of claim 20 wherein the stay is coupled to the second pedicle screw with a variable angle connection.

23. A method of stabilizing a spinal column comprising:
 implanting a first screw in a first vertebral body;
 implanting a second screw in a second vertebral body;
 coupling a dynamic spinal rod between the first screw and the second screw; the dynamic spinal rod comprising:
 a shank with a first end coupled to the first pedicle screw, an opposite second end, and an intermediate section between the first end and the second end;
 a stay coupled to the second pedicle screw, the stay being slideably coupled along the shank; and
 a casing coupled with the intermediate section of the shank and coupled to the stay, the casing being sized to stretch tightly between the shank and the stay and provide a structural connection between the shank and the stay when the stay is near the second end of the shank and sized to extend loosely between the shank and the stay when the stay is moved closer to the first end of the shank; and
 injecting a material between the shank and the stay to dampen contracting movement of the dynamic spinal rod.

24. The method of claim 23 further comprising curing the injected material to change the properties of the material.

* * * * *